US010267510B2

(12) United States Patent
Coleman et al.

(10) Patent No.: US 10,267,510 B2
(45) Date of Patent: Apr. 23, 2019

(54) LIGHT ATTACHMENT FOR INSPECTION TOOL

(71) Applicant: Ullman Devices Corporation, Ridgefield, CT (US)

(72) Inventors: Edward S. Coleman, Ridgefield, CT (US); Qiu Jianping, Hangzhou (CN)

(73) Assignee: Ullman Devices Corporation, Ridgefield, CT (US)

( * ) Notice: Subject to any disclaimer, the term of this patent is extended or adjusted under 35 U.S.C. 154(b) by 26 days.

(21) Appl. No.: 13/633,955

(22) Filed: Oct. 3, 2012

(65) Prior Publication Data

US 2013/0077291 A1 Mar. 28, 2013

Related U.S. Application Data

(63) Continuation of application No. 12/716,509, filed on Mar. 3, 2010, now Pat. No. 8,690,376, which is a continuation-in-part of application No. 12/263,519, filed on Nov. 3, 2008, now Pat. No. 7,980,722, which is a continuation-in-part of application No. 12/174,704, filed on Jul. 17, 2008, now Pat. No. 7,954,972.

(60) Provisional application No. 60/954,515, filed on Aug. 7, 2007.

(51) Int. Cl.
*F21V 33/00* (2006.01)
*G01N 21/88* (2006.01)
*G02B 7/182* (2006.01)

(52) U.S. Cl.
CPC ..... *F21V 33/0084* (2013.01); *G01N 21/8806* (2013.01); *G02B 7/182* (2013.01)

(58) Field of Classification Search
CPC ........ F21W 2131/202; F21W 2131/411; F21V 21/40–21/406
USPC ...... 362/311.11, 296.09, 128, 119, 396, 287, 362/385, 393, 436, 432, 135–142
See application file for complete search history.

(56) References Cited

U.S. PATENT DOCUMENTS

| | | | |
|---|---|---|---|
| 695,338 A | 3/1902 | Paynter et al. | |
| 1,057,820 A * | 4/1913 | Gernsback | 362/135 |
| 1,387,770 A | 8/1921 | Dolbey | |
| 1,426,228 A | 8/1922 | Sloane et al. | |
| 1,555,658 A | 9/1925 | Gongaware | |
| 1,774,331 A * | 8/1930 | Koller | 362/135 |
| 2,185,149 A * | 12/1939 | Hallbauer | 362/156 |
| 2,258,542 A | 10/1941 | Cressaty | |
| 2,645,706 A | 7/1953 | Bowland | |
| 3,714,411 A * | 1/1973 | Waters et al. | 362/137 |
| 4,745,528 A * | 5/1988 | Dieterle | 362/135 |
| 5,458,486 A | 10/1995 | Ballard | |
| 5,568,965 A * | 10/1996 | Eagan | A45D 42/10 362/135 |
| 5,636,918 A * | 6/1997 | Lott | A61B 1/24 362/139 |
| 5,645,706 A | 7/1997 | Matsuda | |
| 5,915,825 A * | 6/1999 | Weister | A61B 1/267 362/138 |

(Continued)

*Primary Examiner* — Julie A Bannan (57) ABSTRACT

A lighted inspection tool includes a mirror having a reflective surface and a back surface, a plastic housing attached to the back surface of the mirror, a light mounted in the housing along a side edge of the housing, a power source housed in the housing and operatively connected to the light member, and a substantially rigid axially telescoping handle pivotably mounted relative to the mirror and the housing.

19 Claims, 4 Drawing Sheets

(56) References Cited

U.S. PATENT DOCUMENTS

| | | | |
|---|---|---|---|
| 5,959,792 A * | 9/1999 | Ibrahim | G02B 7/1821 |
| | | | 248/485 |
| 6,053,315 A | 4/2000 | Yao | |
| 6,550,926 B2 * | 4/2003 | Berger | G02B 7/182 |
| | | | 359/875 |
| 6,698,906 B1 * | 3/2004 | Tally | B25B 9/00 |
| | | | 359/864 |
| 7,001,037 B1 | 2/2006 | Shiao | |
| 7,036,627 B2 | 5/2006 | Costa et al. | |
| 7,090,318 B2 | 8/2006 | Zadro | |
| 7,475,998 B1 * | 1/2009 | Pena | G02B 7/1822 |
| | | | 359/875 |
| 7,954,972 B2 | 6/2011 | Coleman et al. | |
| 7,980,722 B2 | 7/2011 | Coleman et al. | |
| 8,690,376 B2 | 4/2014 | Coleman et al. | |
| 2004/0173498 A1 | 9/2004 | Lee | |
| 2007/0293316 A1 * | 12/2007 | Meyer | 463/37 |

* cited by examiner

LIGHT ATTACHMENT FOR INSPECTION TOOL

CROSS REFERENCE TO RELATED APPLICATION

This application is a continuation of U.S. patent application Ser. No. 12/716,509 filed Mar. 3, 2010, which is a continuation-in-part of U.S. patent application Ser. No. 12/263,519 filed Nov. 3, 2008, now U.S. Pat. No. 7,980,722, which was a continuation-in-part of U.S. patent application Ser. No. 12/174,704 filed Jul. 17, 2008, now U.S. Pat. No. 7,954,972, which claims the benefit of provisional application Ser. No. 60/954,515 filed Aug. 7, 2007.

BACKGROUND OF THE INVENTION

The invention relates to inspection tools and, more particularly, to inspection mirrors such as those that are used by mechanics to view obscured areas of an automobile, and also those which are used by security personnel for example to inspect the underside of automobiles.

Such inspection mirrors allow the user to view areas which would otherwise be difficult or impossible to view. In some instances, such areas are not only obscured from the viewer, but are also dark. In such circumstances, it has been known to position a light member shining parallel to the handle of the device, and onto the mirror to illuminate the area to be viewed. While such an approach does help view the intended area, there is room for improvement in such devices.

It is therefore the primary object of the invention to provide an apparatus to allow better illumination of an area to be inspected.

Other objects and advantages of the invention will appear herein.

SUMMARY OF THE INVENTION

According to the invention, the foregoing objects are attained.

According to one embodiment of the invention, a light attachment is provided for attaching to an inspection tool to illuminate the area to be inspected.

A light assembly is therefore provided for an inspection tool having a mirror, the assembly comprising a housing attached to the mirror; a light member movably attached to the housing; and a power source for the light member.

The mounting bracket is preferably shaped to coincide with the shape of the mirror, preferably round or some other relatively simple shape, and can have two or more clips to hold the bracket to the mirror. A battery for the light member is accessibly stored within the mounting bracket.

With the apparatus according to the invention, light is provided directly on the object to be illuminated, and is not reflected onto the object through the mirror as with prior devices. This provides better illumination and allows more thorough inspection of the object or area to be inspected.

In its broadest sense, the mounting bracket can be attached to the mirror using any method, including glues and adhesives. In addition, the mounting bracket of the first embodiment can have a rim which traverses the circumference or edge of the mounting bracket, and a notch through which the handle of the mirror extends when the mounting bracket and mirror are assembled. Further, the rim may have a plurality of radially spaced notches to allow the mirror to be mounted to the mounting bracket in a plurality of different positions. Rotation of the light member relative to the housing provides additional versatility as well.

In another embodiment, the invention is directed to a lighted inspection tool which comprising a mirror, a housing attached to the mirror, a light member movably attached to the housing and a power source for the light member.

In a further embodiment of the invention, a lighted inspection tool is provided which comprises a mirror having a reflective surface and a back surface, a plastic housing attached to the back surface of the mirror, a light mounted in the housing along a side edge of the housing, a power source housed in the housing and operatively connected to the light member, and a substantially rigid axially telescoping handle pivotably mounted relative to the mirror and the housing.

BRIEF DESCRIPTION OF THE DRAWINGS

A detailed description of preferred embodiments of the invention follows, with reference to the attached drawings, wherein.

DETAILED DESCRIPTION

Figure 1:
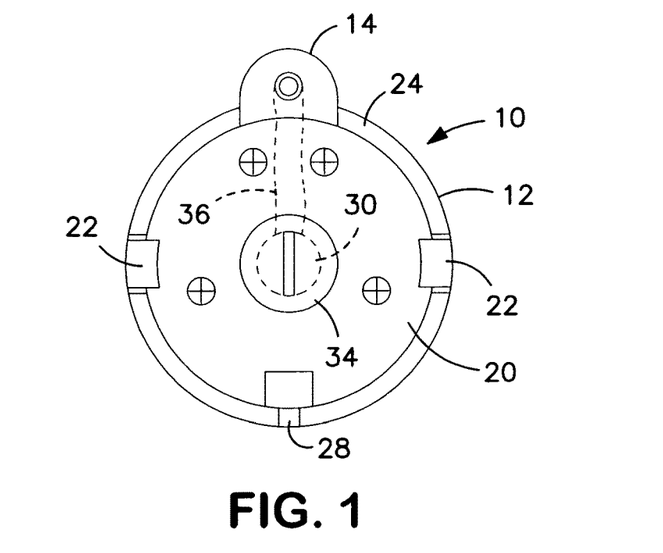
FIG. 1 illustrates an apparatus according to the invention.
Figure 2:
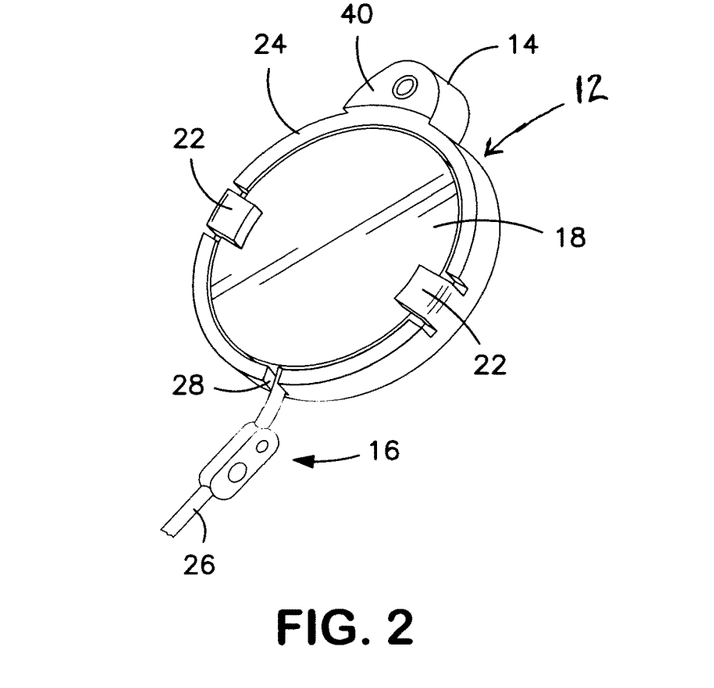
FIG. 2 is a perspective view of the apparatus of the invention installed on an inspection mirror.

FIG. 1 shows an apparatus 10 according to the invention which comprises a mounting bracket generally indicated at 12, and a light member 14 connected to mounting bracket 12. As shown in FIG. 2, mounting bracket 12 is preferably configured for releasable attachment to an inspection mirror tool 16.

Light member 14 can be any suitable light bulb or other light generating device, preferably sufficiently powerful that good illumination can be provided for viewing objects up to several feet from the mirror, from a distance which is also several feet from the mirror. Numerous alternatives are available for the light member as would be well known to a person skilled in this art. Light member 14 can be mounted in mounting bracket 12 in any suitable manner, preferably such that the light bulb itself can be replaced as needed.

Mounting bracket 12 is preferably a structure shaped to fit around the mirror portion 18 of inspection mirror tool 16. FIG. 2 shows a round mirror portion 18, and thus in this embodiment mounting bracket 12 is also substantially round in shape. As shown, mounting bracket 12 can have a body portion 20 sized to be held behind mirror portion 18, and this portion 20 preferably has at least one and preferably at least two clips 22 for snapping past the front edge of mirror portion 18 to hold bracket 12 in place with respect to mirror portion 18. Mounting bracket 12 can also have a forwardly extending lip or rim 24 which is sized to fit around the outer edge or circumference of mirror portion 18, and thereby stabilize mounting bracket 12 relative to mirror portion 18 during use. Inspection mirror tool 16 typically has a handle 26 which can be extended and used to position mirror portion 18 in a desired location to view desired areas or objects. Lip 24 preferably has a notch 28 in lip 24 sized to accept handle 26.

According to the invention, two clips 22 can preferably be positioned at opposite sides of mounting bracket 12 as shown, with light member 14 at a top area of mounting bracket 12, and with notch 28 positioned opposite from light member 12. In this configuration, apparatus mounting bracket 12 can be secured to mirror portion 18 as desired, and light directed along a focal axis of mirror portion 18 also as desired.

Light member 14 can be powered from a battery 30, which can be wired to light member 14, preferably through a switch 32 (FIGS. 3 and 4) to allow light member 14 to be selectively powered off and on. Battery 30 can suitably be stored within a compartment inside mounting bracket 12, and an access door 34 can be provided in mounting bracket 12 to allow battery 30 to be accessed and changed as necessary.

Figure 3:
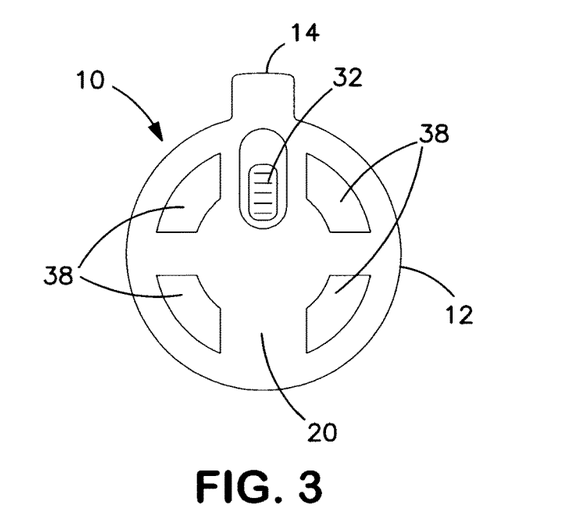
FIG. 3 is a rear view of the apparatus of the present invention.

FIG. 3 shows a rear view of apparatus 10 according to the invention, and shows switch 32 for powering the light on and off. Also, it should be appreciated that mounting bracket 12 in this embodiment is defined by a front wall and a rear wall, and that these walls define the compartment for holding battery 30, as well as the wiring 36 which connects battery 30 and light member 14. FIG. 3 shows one embodiment of the rear wall of apparatus 10, and this rear wall can have a plurality of cutouts 38 which serve to reduce the amount of material required to manufacture mounting bracket 12, which can suitably be injection molded from plastic.

Figure 4:
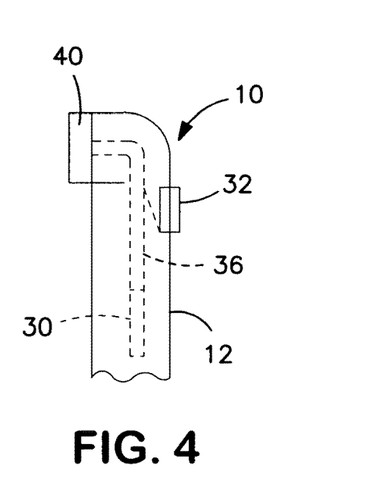
FIG. 4 is a side view of a portion of the apparatus of the invention showing internal wiring of the light member.

FIG. 4 shows a side view and schematically illustrates battery 30, wiring 36 and switch 32 which are used according to the invention to selectively turn light member 14 on and off. FIGS. 2 and 4 show that light member 14 can be surrounded by a housing 40 which extends forwardly beyond mirror 18 and lip 24. This housing 40 serves to protect the light bulb within light member 14 from being damaged by incidental contact with various objects during use of apparatus 10.

Figure 5:
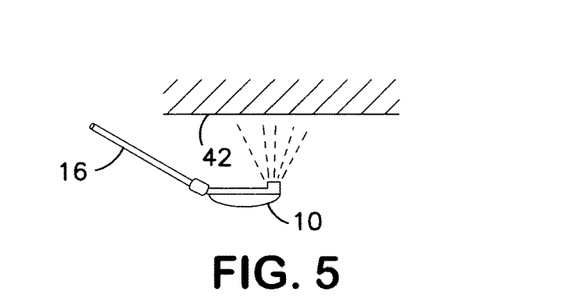
FIG. 5 shows an apparatus according to the invention attached to a mirror and illuminating an otherwise obscured surface.

FIG. 5 shows apparatus 10 secured to an inspection mirror tool 16 and being used to illuminate and view a surface 42. This use of apparatus 10 according to the invention can as indicated above serve to allow inspection of the underside of vehicles, or otherwise obscured areas in an engine compartment and the like.

Figure 6:
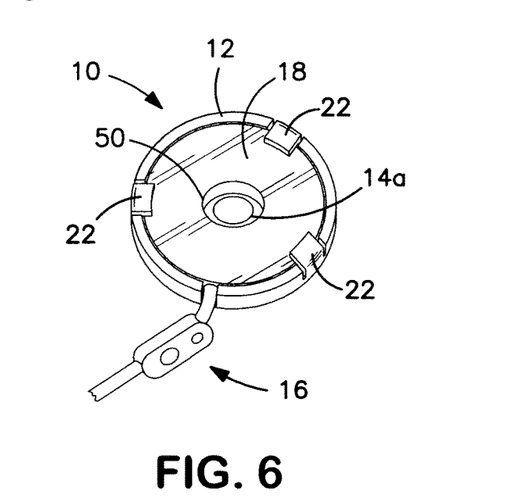
FIG. 6 shows an alternate embodiment of the invention.

FIG. 6 shows an alternate embodiment of apparatus 10 wherein light member 14a is centrally located on holder 12, and mirror portion 18 has a central opening or hole 50 through which light member 14a shines during use. The housing of bracket 12 can be defined by two spaced walls in similar fashion to the embodiment of FIGS. 1-5, with battery and wiring positioned internally, the battery being changeable, and a switch being positioned for powering light member 14a on and off as desired. In this embodiment, while the mirror portion 18 is slightly complicated by the need for central opening 50, the advantage gained by this extra effort is a central location of light member 14a, which serves to more directly and properly illuminate an area to be viewed. Bracket 12 in this embodiment snaps onto and off of mirror portion 18 in similar fashion to the embodiment of FIGS. 1-5.

Figure 7:
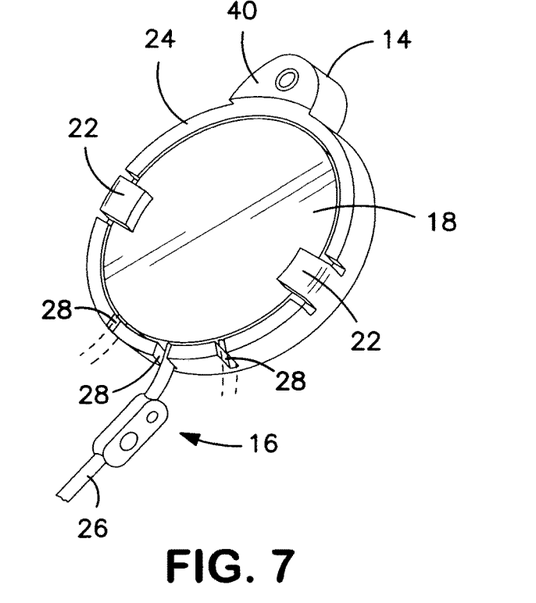
FIG. 7 shows an alternate embodiment of the invention, wherein the mounting bracket has a plurality of notches for accommodating the handle of the mirror in different positions.

Turning to FIG. 7, a further embodiment of the present invention is illustrated, wherein mounting bracket 10 has a plurality of spaced notches 28, in this instance based around circumferential rim 24, to accommodate handle 26 in a plurality of different positions between the mirror and the mounting bracket. In this manner, light member 14 can be positioned in different locations with respect to the handle of the device. It is noted that FIG. 2 shows this embodiment with a round mirror and with notches 28 positioned radially spaced along a portion of the lip accommodating the round mirror. It should be appreciated that this plurality of notches could be utilized in other-shaped mirrors and mounting brackets, well within the broad scope of the present invention.

Figure 8:
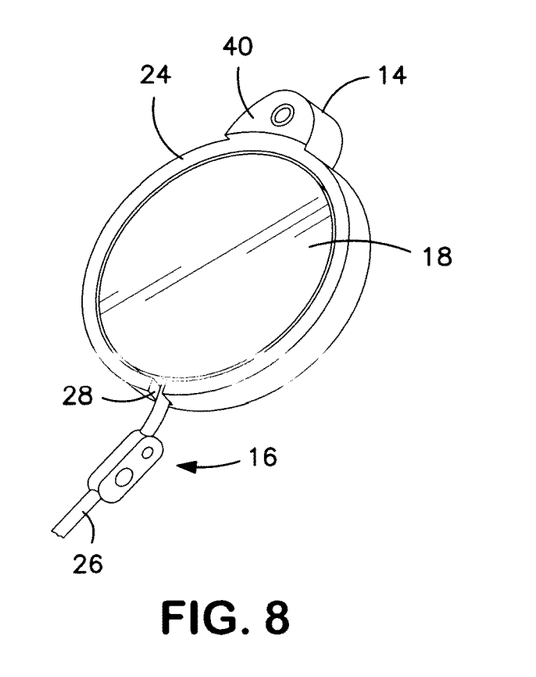
FIG. 8 shows a simplified embodiment of the present invention wherein the mounting bracket is attached to the mirror, for example using glue or some other type of adhesive, without clips.

FIG. 8 shows a further alternate embodiment of the present invention wherein mounting bracket 10 is not releasably connected to the mirror. That is, mounting bracket 10 is configured for other types of attachments to mirror 18, for example involving glue or adhesives for securing mounting bracket 24 to mirror 18. In this embodiment, as well, the mounting bracket and mirror preferably match each other in shape, and could be round, square, triangular, rectangular or the like. It should be appreciated that the simplified structure, while removing the mounting brackets mentioned in earlier embodiments, results in a more permanent structure, but also in potentially reduced costs for the molding of the mounting bracket part, which can now be held in place through either a permanent press fit with the mirror, or with adhesives, or combinations thereof.

Figure 9:
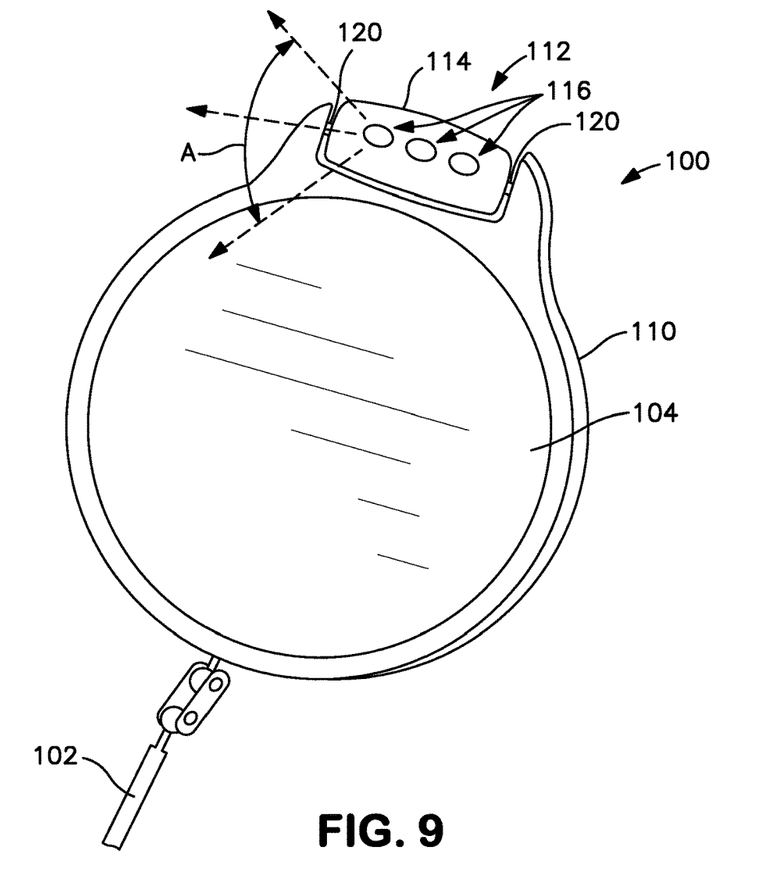
FIGS. 9 and 10 show a further embodiment of the invention including a rotatable light fixture.

FIG. 9 shows a further embodiment of a lighted inspection device in accordance with the present invention. As shown, lighted inspection device 100 has a handle 102 and inspection mirror 104, with inspection mirror 104 being connected to handle 102 through a pivot device which is well known to persons skilled in the art. The pivot device allows adjustment of mirror 104 relative to handle 102. Handle 102 can have a telescoping shaft incorporated therein such that mirror 104 can be extended a distance from the hand-held portion of handle 102.

In accordance with this embodiment of the invention, mounted around mirror 104 is a housing 110 to which a light member 112 is movably attached. Housing 110, as with the embodiments discussed above, contains a compartment for batteries and a switch and wiring connecting the battery to the light so that the light can be selectively turned on and off as appropriate. These features are as described and illustrated in other embodiments above.

In this embodiment, light member 112 is mounted to housing 110 in a rotatable fashion such that light member 112 can be rotated or angled to direct light along a path which is movable with respect to the plane of the mirror of the device. This provides additional flexibility in illuminating specific areas to be inspected.

In this embodiment, light member 112 can have a light housing 114 containing one or more lights 116, and light housing 114 is advantageously rotatably mounted relative to housing 110, for example a pair of pivots or axles which define pivot points 120. In this regard, the wiring for operating lights 116 within light housing 114 can advantageously pass through the pivot points 120 between the light housing 114 and the housing 110.

Figure 10:
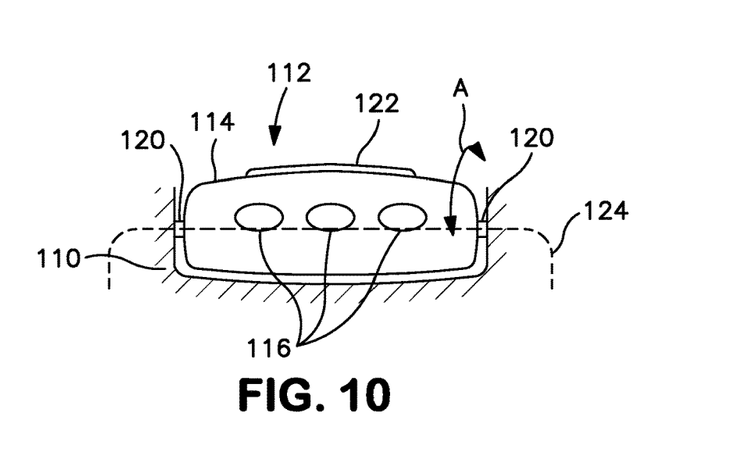

As shown also in FIG. 10, the rotatable light member 112 is mounted at an edge of the mirror which is opposite to the handle 102, and the light member is preferably mounted for rotation about an axis which, when the mirror is in a straight position with respect to the handle, is substantially perpendicular to the axis of the handle. This axis may also and/or alternatively be substantially parallel to a plane of mirror 104. While any degree of motion of the light with respect to the mirror would be desirable, this positioning of the axis of rotation of the light member with respect to the mirror is particularly desirable as providing for maximum usage of the different possible angles of the light member.

The movement of light housing 114 relative to housing 110 is shown in FIGS. 9 and 10 by the arrows A illustrating rotation. This allows light to be directed in a desired direction with respect to the plane of mirror 104.

FIG. 10 also shows a small ridge 122 on light housing 114 which can advantageously extend radially outward from light housing 114 and can be used to gain traction on light housing while attempting to rotate light housing 114 to a desired position.

FIG. 10 further schematically illustrates wiring 124 passing from a housing mounted switch and battery (as shown in FIGS. 1 and 3) through hollow pivot connections 120 to light bulbs 116. In this way rotation of light housing 114 relative to housing 110 does not interfere with powering of light bulbs 116.

It should be appreciated that this description has been provided in terms of a preferred embodiment of the invention, and that various details and aspects of the embodiment described could be modified by a person skilled in the art. The present invention is deemed to include such modifications, and the broad scope of the present invention is not limited by the specific details of this description.

The invention claimed is:

1. A lighted inspection tool for inspecting obstructed dark areas, comprising:
    a mirror;
    a housing attached to the mirror, a rim of the housing surrounding as least a portion of an edge of the mirror, the rim defining a notch;
    a light member mounted in the housing at a first position about the mirror;
    a power source housed in the housing and operatively connected to the light member; and
    a handle having a substantially rigid axially telescoping shaft, a coupling portion; and a pivot joint between the telescoping shaft and the coupling portion, the coupling portion of the handle coupled to the housing within the notch at a second position about the mirror, the second position substantially opposite to the first position, the telescoping shaft of the handle pivotably, mounted relative to the coupling portion of the handle and the mirror about the pivot joint.

2. The lighted inspection tool of claim 1, wherein:
    the housing defines an interior space; and
    the power source comprises a battery holder positioned within the interior space.

3. The lighted inspection tool of claim 1, wherein the mirror is facing a front side of the housing, the lighted inspection tool further comprising:
    wiring from the power source to the light member; and
    a switch mounted on a back side of the housing, the back side of the housing opposite the front side of the housing.

4. The lighted inspection tool of claim 3, wherein the light member is mounted along a side edge of the housing.

5. The lighted inspection tool of claim 1, wherein the light member is rotatable around an axis substantially parallel to a plane of the mirror, whereby light can be directed from the light member in different directions with respect to the mirror.

6. The lighted inspection tool of claim 1, wherein the light member includes a substantially cylindrical light housing pivotably mounted to the housing, and at least one light generating device mounted in the light housing.

7. The lighted inspection tool of claim 1, wherein the housing is made of plastic and includes a plurality of clips to attach the housing to the mirror, the plurality of clips extending inwardly from the rim over the edge of the mirror.

8. The lighted inspection tool of claim 1, wherein the light member comprises a plurality of light generating devices mounted in the housing.

9. A lighted inspection tool for inspecting obstructed dark areas, comprising:
    a mirror having a reflective front surface and a back surface;
    a plastic housing attached to the back surface of the mirror, the plastic housing including a rim that surrounds a front edge of the mirror, the rim defining an opening at a second position along a side edge of the plastic housing;
    a light member mounted in the plastic housing at a first position along the side edge of the plastic housing;
    a power source housed in the plastic housing and operatively connected to the light member; and
    a substantially rigid axially telescoping handle pivotably mounted relative to the mirror and the plastic housing by a pivot joint that is spaced apart from the plastic housing by a coupling portion, wherein the coupling portion of the handle is coupled to the plastic housing within the opening at the second position along the side edge of the plastic housing.

10. A method for illuminating an obstructed dark area, comprising:
    moving a switch on a back side of a housing of a lighted inspection tool to allow transmission of power from a power source within the housing to a light member coupled at a first position along a side edge of the housing, the lighted inspection tool having a mirror coupled to a front side of the housing and a handle having a telescoping shaft pivotably mounted relative to the mirror and the housing by a pivot joint, the pivot joint coupled to the housing at a second position along the side edge of the housing within a notch defined by a rim of the front side of the housing that surrounds the mirror such that the light is mounted in the housing substantially opposite to the handle;
    extending the telescoping shaft of the handle; and
    placing the mirror at the obstructed dark area, whereby the light allows inspection of the obstructed dark area.

11. The lighted inspection tool of claim 1, wherein the notch is one of a plurality of notches defined by the rim of the housing.

12. The lighted inspection tool of claim 1, wherein a shape of the mirror is any one of circular, square, or rectangular.

13. The lighted inspection tool of claim 9, wherein the mirror is facing a front side of the plastic housing, the lighted inspection tool further comprising:
    wiring from the power source to the light member; and
    a switch mounted on a back side of the plastic housing, the back side of the plastic housing opposite the front side of the plastic housing.

14. The lighted inspection tool of claim 9, wherein the pivot joint includes at least one ball joint.

15. The lighted inspection tool of claim 9, wherein a shape of the side edge of the plastic housing is any one of circular, square, or rectangular.

16. The method of claim 10, further comprising:
    rotating the mirror relative to the telescoping shaft of the handle via the pivot joint.

17. The method of claim 10, wherein a shape of the mirror is any one of circular, square, or rectangular.

18. The lighted inspection tool of claim 9, wherein the opening is one of a plurality of openings defined by the rim of the plastic housing.

19. The method of claim 10, wherein the notch is one of a plurality of notches defined by the rim of the housing.

\* \* \* \* \*

UNITED STATES PATENT AND TRADEMARK OFFICE
CERTIFICATE OF CORRECTION

Page 1 of 1

PATENT NO. : 10,267,510 B2
APPLICATION NO. : 13/633955
DATED : April 23, 2019
INVENTOR(S) : Edward S. Coleman et al.

It is certified that error appears in the above-identified patent and that said Letters Patent is hereby corrected as shown below:

In the Claims

Claim 1, Line 5; Column 5, Line 38 – change "as least" to --at least--

Signed and Sealed this
Fourth Day of June, 2019

Andrei Iancu
*Director of the United States Patent and Trademark Office*